(12) United States Patent
Lew et al.

(10) Patent No.: US 10,364,209 B2
(45) Date of Patent: Jul. 30, 2019

(54) METHODS FOR PREPARING OILS CONTAINING AT LEAST 2% ALKYL-BRANCHING ON THE HYDROCARBON CHAIN

(71) Applicant: The United States of America, as Represented by the Secretary of Agriculture, Washington, DC (US)

(72) Inventors: Helen N. Lew, Wyndmoor, PA (US); Renee J. Latona, Warminster, PA (US); Majher I. Sarker, Wyndmoor, PA (US); Robert A. Moreau, Quakertown, PA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/117,266

(22) Filed: Aug. 30, 2018

(65) Prior Publication Data

US 2019/0062672 A1    Feb. 28, 2019

Related U.S. Application Data

(60) Provisional application No. 62/552,684, filed on Aug. 31, 2017, provisional application No. 62/564,592, filed on Sep. 28, 2017.

(51) Int. Cl.
*C11C 3/00* (2006.01)
*C07C 51/353* (2006.01)
(Continued)

(52) U.S. Cl.
CPC .............. *C07C 67/333* (2013.01); *B01J 29/06* (2013.01); *B01J 29/70* (2013.01); *B01J 29/7007* (2013.01);
(Continued)

(58) Field of Classification Search
CPC ....... C07C 67/333; C07C 51/353; C11C 3/00; B01J 29/06; B01J 29/65; B01J 29/70; B01J 29/7007
See application file for complete search history.

(56) References Cited

U.S. PATENT DOCUMENTS

| | | | |
|---|---|---|---|
| 6,455,716 B2 * | 9/2002 | Kenneally | C07C 51/353 502/77 |
| 6,723,862 B2 * | 4/2004 | Shuguang | B01J 29/041 423/277 |

(Continued)

*Primary Examiner* — Yate' K Cutliff
(74) *Attorney, Agent, or Firm* — G. Byron Stover; John D. Fado; Gail E. Poulos

(57) ABSTRACT

A method for preparing triglyceride oils containing at least 2% branching on the hydrocarbon chain, said method involving subjecting in a pressurized container (a) a feedstock containing unsaturated fatty acids attached to a glycerol backbone having 6 to 25 carbon atoms or mixtures thereof, (b) modified zeolite, and (c) water or alcohol in the presence of an inert atmosphere (e.g., at a temperature of about 150° C. to about 350° C. and a pressure of about 10 to about 300 psi for about 24 to about 72 hours) to produce triglycerides containing at least 2% branching (and optionally isolating said triglycerides containing at least 2% branching and optionally purifying the isolated triglycerides containing at least 2% branching); wherein said modified zeolite has been calcined at about 760° C. to about 840° C. for about 20 to about 28 hours, then placed in about 1N HCl at about 50° C. to about 60° C. for about 20 to about 28 hours and washed with water until the pH is neutral.

5 Claims, 4 Drawing Sheets

(51) Int. Cl.
*C07C 67/333* (2006.01)
*B01J 29/70* (2006.01)
*B01J 29/06* (2006.01)
*C11C 3/10* (2006.01)

(52) U.S. Cl.
CPC ............. *C07C 51/353* (2013.01); *C11C 3/00* (2013.01); *C11C 3/10* (2013.01)

(56) References Cited

U.S. PATENT DOCUMENTS

| | | | | |
|---|---|---|---|---|
| 6,831,184 | B2 * | 12/2004 | Zhang | B01J 29/084 502/77 |
| 9,115,076 | B2 * | 8/2015 | Ngo | C07C 67/333 |
| 2011/0263884 | A1 * | 10/2011 | Ngo | B01J 29/06 554/154 |

* cited by examiner

METHODS FOR PREPARING OILS CONTAINING AT LEAST 2% ALKYL-BRANCHING ON THE HYDROCARBON CHAIN

REFERENCE TO RELATED APPLICATION

This application claims the benefit of U.S. Provisional Application No. 62/552,684, filed 31 Aug. 2017, and U.S. Provisional Application No. 62/564,592, filed 28 Sep. 2017, which are incorporated herein by reference in their entirety.

BACKGROUND OF THE INVENTION

Disclosed herein are methods for preparing triglyceride oils containing at least 2% branching on the hydrocarbon chain, said method involving subjecting in a pressurized container (a) a feedstock containing unsaturated fatty acids attached to a glycerol backbone having 6 to 25 carbon atoms or mixtures thereof, (b) modified zeolite, and (c) water or alcohol in the presence of an inert atmosphere (e.g., at a temperature of about 150° C. to about 350° C. and a pressure of about 10 to about 300 psi for about 24 to about 72 hours) to produce triglycerides containing at least 2% branching (and optionally isolating the triglycerides containing at least 2% branching and optionally purifying the isolated triglycerides containing at least 2% branching); wherein the modified zeolite has been calcined at about 760° C. to about 840° C. for about 20 to about 28 hours, then placed in about 1N HCl at about 50° C. to about 60° C. for about 20 to about 28 hours and washed with water until the pH is neutral.

Petroleum-based materials, while generally cheaper to produce than bio-based products, tend to resist the typical degradation found in nature resulting in problems in their waste management (Thomas, C. E. S., Lecture Notes in Energy, 35: 1-8 (2017)). For this reason, strict environmental regulations were imposed upon the use of petroleum-based materials. Particularly, in the lubrication field, there have been tremendous health concerns from the use of synthetic lubricants (Adhvaryu, A., et al., Ind. Crops Prod., 21: 113-119 (2005); Nagendramma, P., and S. Kaul, Renew. Sustain. Energy Rev., 16: 764-774 (2012)). These products have been shown to be harmful to the environment and have been found in the water, soil and air (Adhvaryu, A., et al., 2012; Nagendramma, P., and S. Kaul, 2012). Therefore, further development of novel technologies to convert bio-based oils into value-added bio-based products would reduce global tension over petroleum resources and mitigate climate change (Biermann, U., et al., Angew. Chem. Int. Ed., 39: 2206-2224 (2000)).

Vegetable oils (i.e., triglycerides) are currently used in the industry as bio-lubricants. Unfortunately, these oils are not stable at high temperatures and are viscous at low temperatures (Battersby, N. S., et al., Chemosphere, 24: 1998-2000 (1992); Becker, R., and A. Knorr, Lubr. Sci., 8: 95-117 (1996)). These drawbacks have prevented them from being widely adopted. Modification of triglycerides is the most direct way to overcome these two drawbacks. Particularly, branching on the carbon chains of the triglycerides can potentially reduce their freezing points because of the disruption of the molecular packing of the oils. This reduces the probability of crystal formation in cold climates. For example, the melting point of the methyl ester of palmitic acid, a linear 16 carbon saturated fatty acid, is 30° C. (Knothe, G., and R. O. Dunn, JOACS, 86:843-856 (2009)). On the other hand, the 16 carbon fatty acid 15 carbons long chain with a methyl branch at carbon 14 has a melting point of 16.8° C. (Knothe, G., and R. O. Dunn, 2009). The melting point falls progressively as the position of the methyl recedes from the ends of the molecule. The ester branched-chain canola oils prepared from a two-step heterogeneous process (epoxidation followed by ring opening) also showed a significantly lower pour-point property after modification (Madankar, C. S., et al., Ind. Crops and Prod., 44: 139-144 (2013)). These modified canola oils maintained a stable lubricating film to prevent the wear of metal surfaces (Madankar, C. S., et al., 2013). Palm oils with high saturation level (50% fatty acids (FA)) are not widely used as lubricants. Pillai et al. (Pillai, P. K. S, et al., Ind. Crops Prod., 84: 205-223 (2016)) expanded the use of these oils by using a cross metathesis method followed by epoxidation and hydroxylation to produce functionalized polyol palm oils. These polyol products were found to have low-melting point properties (Pillai, P. K. S, et al., 2016)). Isomerization of oils (in the form of FA) to introduce methyl-branching on the alkyl FA was explored by several research groups to improve the low temperature property of the materials (U.S. Pat. No. 6,946,567; U.S. Pat. No. 5,677,473; EP 0774451A1). Particularly, the work on the zeolite-Lewis base combination isomerization process was found to be the most efficient system to produce methyl-branched-chain FA (MBC-FA) to date (Ngo, H. L., et al., Eur. J. Lipid Sci. Technol., 114: 213-221 (2012); U.S. Pat. No. 9,115,076). The products were reported to have excellent low temperature properties and good lubricity properties (Ngo, H. L., et al., Eur. J. Lipid Sci. Technol., 113: 180-188 (2011); Ngo, H., et al., Eur. J. Lipid Sci. Technol., 118: 1915-1925 (2016)). In addition, this isomerization process generated low by-product levels and have these attractive advantages over prior systems, including (1) ready recovery by filtration, (2) reuse 20 recycles having been achieved without significant loss of activity or selectivity, and (3) an absence of added organic solvent (Ngo, H. L., Eur. J. Lipid Sci. Technol., 116: 645-652 (2014)).

To increase the functional fluid consumption of branching bio-based products, we developed a new fatty acid isomerization system. We have developed methods to convert of triglycerides (e.g., natural plant oils) containing unsaturated hydrocarbon chains using a modified zeolite as a heterogeneous catalyst into triglycerides generally containing at least about 2% branching and up to about 30% branching (methyl-branched-chain triglycerides (MBC-TG)) which can be used, for example, for lubrication purposes. The isomerization generally involved the presence of a modified zeolite (e.g., $H^+$-BETA) catalyst and water (or alcohol) co-catalyst at various reaction temperatures and reaction times.

SUMMARY OF THE INVENTION

Disclosed herein are methods for preparing triglyceride oils containing at least 2% branching on the hydrocarbon chain, said method involving subjecting in a pressurized container (a) a feedstock containing unsaturated fatty acids attached to a glycerol backbone having 6 to 25 carbon atoms or mixtures thereof, (b) modified zeolite, and (c) water or alcohol in the presence of an inert atmosphere (e.g., at a temperature of about 150° C. to about 350° C. and a pressure of about 10 to about 300 psi for about 24 to about 72 hours) to produce triglycerides containing at least 2% branching (and optionally isolating the triglycerides containing at least 2% branching and optionally purifying the isolated triglycerides containing at least 2% branching); wherein the modified zeolite has been calcined at about 760° C. to about 840°

C. for about 20 to about 28 hours, then placed in about 1N HCl at about 50° C. to about 60° C. for about 20 to about 28 hours and washed with water until the pH is neutral.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

DETAILED DESCRIPTION OF THE INVENTION

Disclosed herein are methods for preparing oils (i.e., triglycerides) containing at least about 2% (e.g., at least 2%) branching on the hydrocarbon chain, involving subjecting in a pressurized container (a) a feedstock (e.g., unsaturated hydrocarbon chain attached to a glycerol backbone having 6 to 25 carbon atoms or mixtures thereof), (b) modified zeolite (as described herein), and (c) water or alcohol (e.g., methanol, ethanol) in the presence of an inert atmosphere (e.g., argon (Ar)) at a temperature of about 150° C. to about 350° C. (e.g., 150° C. to 350° C.; preferably about 175° C. to about 325° C. (e.g., 175° C. to 325° C.); more preferably about 200° C. to about 300° C. (e.g., 200° C. to 300° C.)) and a pressure of about 10 to about 300 psi (e.g., 10 to 300 psi; preferably about 10 to about 200psi (e.g., 10 to 200 psi); more preferably about 10 to about 100psi (e.g., 10 to 100 psi)) for about 24 to about 72 hours (e.g., 24 to 72 hours; preferably 24 to about 48 hours (e.g., 24 to 48 hours); preferably 24 to about 36 hours (e.g., 24 to 36 hours); most preferably about 24 hours (e.g., 24 hours)) to produce triglycerides containing at least about 2% (e.g., at least 2%) branching on the hydrocarbon chain, optionally isolating (e.g., by distillation) the triglycerides containing at least 2% branching, and optionally purifying (e.g., with wiped-film distillation device) the isolated triglycerides containing at least about 2% branching (e.g., at least 2%). The modified zeolite has been calcined at about 760° C. to about 840° C. (e.g., 760° C. to 840° C.; preferably 780° C. to 820° C. (e.g., 780° C. to 820° C.); preferably 790° C. to 810° C. (e.g., 790° C. to 810° C.); most preferably about 800° C. (e.g., 800° C.)) for about 20 to about 28 hours (e.g., 20 to 28 hours; preferably about 22 to about 26 hours (e.g., 22 to 26 hours); more preferably about 24 hours (e.g., 24 hours), then placed in about 1N HCl at about 50° C. to about 60° C. (e.g., 50° C. to 60° C.; preferably about 55° C. (e.g., 55° C.)) for about 20 to about 28 hours (e.g., 20 to 28 hours; preferably about 22 to about 26 hours (e.g., 22 to 26 hours); more preferably about 24 hours (e.g., 24 hours)) and washed with water until the pH is neutral. The synthesized products were characterized by gas chromatography (GC), GC-mass spectroscopy (GC-MS), and high performance liquid chromatography (HPLC).

Figure 1:
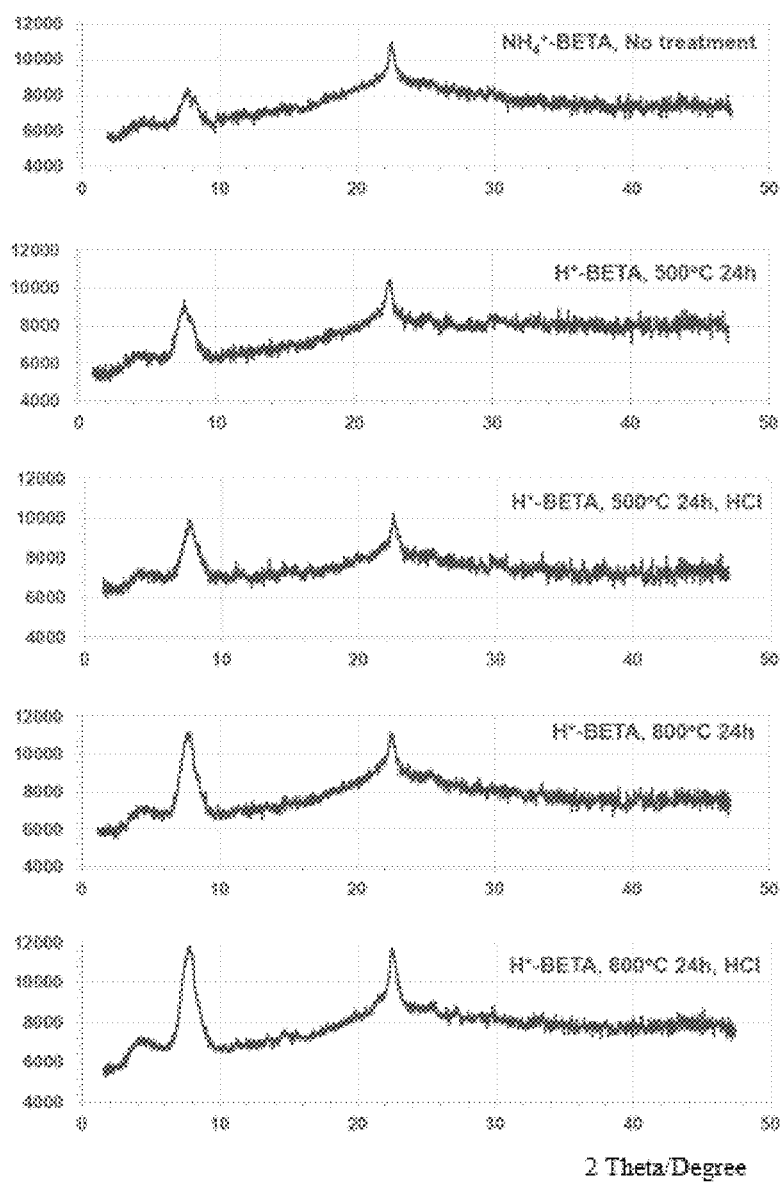
FIG. 1 shows powder x-ray diffraction (PXRD) of modified and unmodified BETA zeolite catalysts as described below.

These isomerized results were surprising in terms of the maximum amounts of branched glycerides formed (Table 3, Entry 9). Without being bound by theory, this could be because the reactions were occurring at the external surfaces of the zeolite as the feedstock (e.g., triglycerides such as sunflower oil) was probably too bulky to undergo rearrangement of the double bond in the internal channels of the zeolites. This speculation is reasonable as the yield of the product could not be obtained beyond 20 wt %, which, without being bound by theory, could be due to either limited amount of external acid sites on the zeolite available for isomerization or that the complex well-defined zeolite framework made it challenging for the oil to access. The latter was supported by the PXRD results (FIG. 1) which showed the zeolite framework was still highly crystalline even when this BETA zeolite was heated at 800° C.; there was very little effect on the crystallinity of the solids.

Examples of zeolitic materials employable in the present invention include, but are not limited to, zeolites having the following framework structures: CON, DFO, FAU, AFS, AFY, BEA, BPH, EMT, GME, MOR, and the like. Zeolites usefully employed in this embodiment of the invention are typically acidic zeolites with or without metal ions, in addition to protons. Specific examples of zeolite structures include, but are not limited to, faujasite, mordenite, USY, MFI, Mor, Y and Beta types. Types of zeolites which can be used include Class A zeolites such as CP814E, BETA, ZSMS, Zeolite Y, and Ferrierite zeolites with Silica/Alumina (Si/Al) ratio between 5 and 50.

The oil (triglycerides) used as the starting material is generally an unbranched-chain oil having unsaturated bonds and a total carbon number of 10 to 25, preferably a total carbon number of 16 to 22 (e.g., sunflower oil). Considering industrial applications, it is preferable that the major component of the starting material is an oil with unsaturated hydrocarbon chain for the synthesis of branched chain oils for use in, for example, coating materials, corrosion inhibitors, lubricants, etc. With respect to the degree of unsaturation (i.e., the number of unsaturated carbon-carbon bonds), any unsaturated hydrocarbon may be used as long as one or more such bonds are present in the molecule. Preferably, the number of unsaturated bonds is generally 1 to 3. Without being bound by theory, the presence of an unsaturated bond in the molecule causes the formation of a carbocation as an intermediate, thereby facilitating the isomerization reaction.

Unbranched-chain (or unsaturated linear-chain) oil which may be used include, for example, palm oil, safflower oil, sunflower oil, tall oil, rapeseed oil, soybean oil, fish oil, or the like. A mixture that may be used as the starting material is, for example, a mixture containing two or more of these unsaturated linear-chain oils, and the like. In the case of a mixture, the content of the above-mentioned unsaturated oils is generally not less than about 40% by weight (e.g., not less than 40% by weight), preferably not less than about 50% by weight (e.g., not less than 50% by weight), preferably not less than about 60% by weight (e.g., not less than 60% by weight), preferably not less than about 70% by weight (e.g., not less than 70% by weight), and most preferably not less than about 80% by weight (e.g., not less than 80% by weight) in view of reaction rate and yield. These amounts are not meant to be limiting, and increments between the recited percentages are specifically envisioned as part of the invention.

Water used in the reaction is generally distilled water, although an alcohol (e.g., C1-C4) can be used.

The reaction apparatus used is preferably pressurized (e.g., an autoclave) because a pressurized reaction system is preferred. The atmosphere in the autoclave is preferably replaced with inert atmosphere such as nitrogen or argon.

The oil products generally contain at least about 2% (e.g., at least 2%) branching on the hydrocarbon chain, preferably at least about 3% (e.g., at least 3%), preferably at least about 4% (e.g., at least 4%), preferably at least about 5% (e.g., at least 5%), preferably at least about 6% (e.g., at least 6%), preferably at least about 7% (e.g., at least 7%), preferably at least about 8% (e.g., at least 8%), preferably at least about 9% (e.g., at least 9%), preferably at least about 10% (e.g., at least 10%), preferably at least about 11% (e.g., at least 11%), preferably at least about 12% (e.g., at least 12%), preferably at least about 13% (e.g., at least 13%), preferably at least about 14% (e.g., at least 14%), preferably at least about 15% (e.g., at least 15%), preferably at least about 16% (e.g., at least 16%), preferably at least about 17% (e.g., at least 17%), preferably at least about 18% (e.g., at least 18%), preferably at least about 19% (e.g., at least 19%), preferably at least about 20% (e.g., at least 20%), preferably about 20% (e.g., 20%), preferably about 21% (e.g., 21%).

"Optional" or "optionally" means that the subsequently described event or circumstance may or may not occur, and that the description includes instances in which said event or circumstance occurs and instances where it does not. For example, the phrase "optionally adding a second zeolite" means that the method may or may not involve adding a second zeolite and that this description includes methods that involve and do not involve adding a second zeolite.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Materials: Sunflower oil (standard, 83.5 wt % oleic acid) was a gift from Muller Lubrication (Tyler, Tex.). Zeolite ammonium BETA (CP814E) was from Zeolyst International (Kansas City, Kans.). 5 wt % palladium on carbon catalyst (Pd/C) was from Pressure Chemical Co. (Pittsburgh, Pa.). Hydrochloric acid (HCl), sulfuric acid, phenolphthalein, and alumina (neutral, 60-325 Mesh) were purchased from Thermo Fisher Scientific (Pittsburgh, Pa.). Sodium methoxide solution (30% in methanol) was from Evonik Corporation (Theodore, Ala.).

Figure 2:
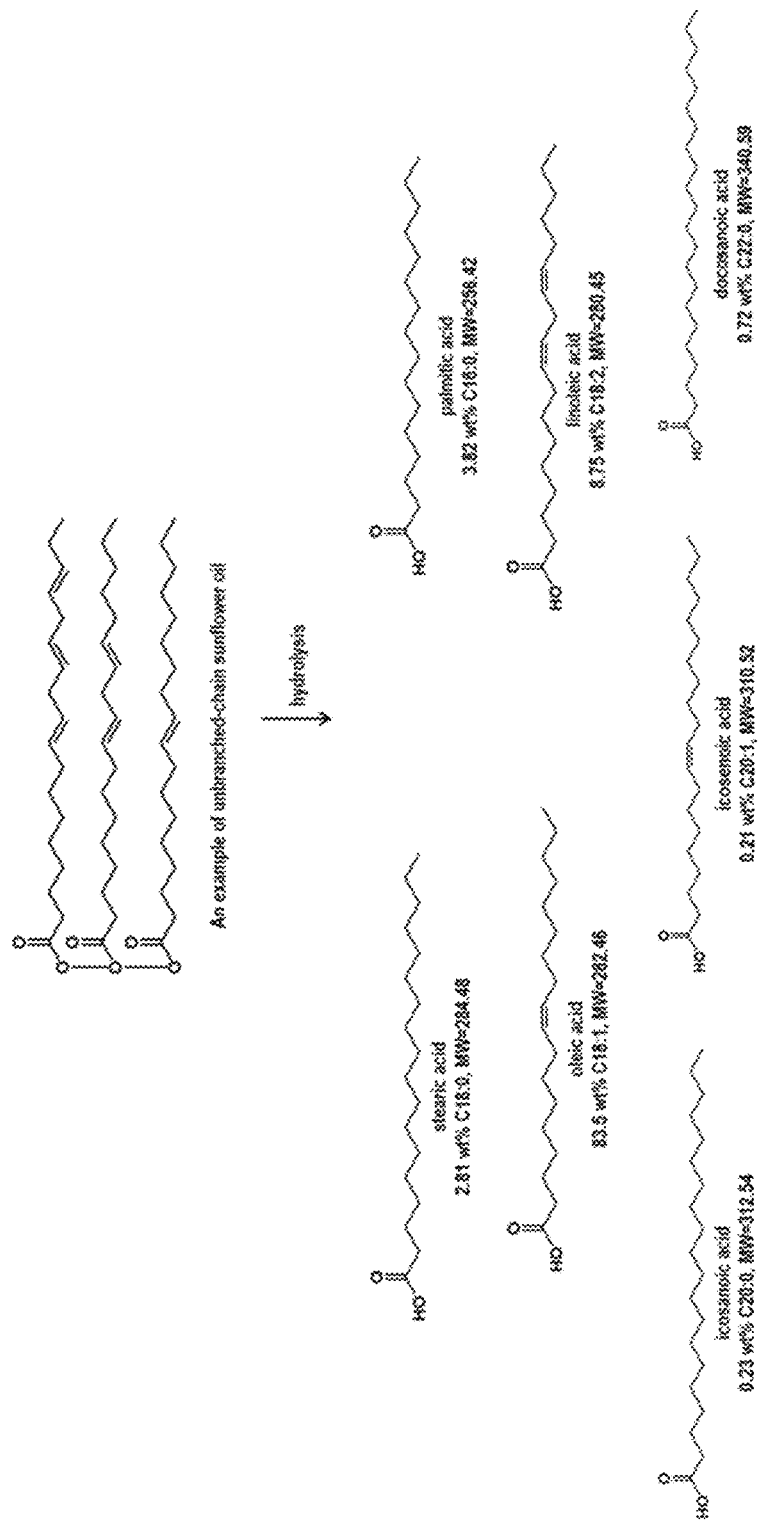
FIG. 2 shows one scheme for the hydrolysis of sunflower oil to sunflower fatty acids as described below.

Experimental procedures and analytical methods. Determination of the sunflower oil fatty acid compositions: 10 g of sunflower oil was added to a vial along with 100 mg of sodium methoxide solution (30%) and 3.6 mL of methanol (FIG. 2). The vial was sealed with Teflon™ tape and placed on a heating mantle at 60° C. for 60 minutes. After 60 minutes, the vial was removed and cooled to room temperature (RT). The sample was transferred to a round bottom flask and the methanol was removed under reduced pressure. 1.0 mL of acetic acid was added to the flask and then 30 mL of hexanes was added. The mixture was transferred to a separatory funnel and washed twice with water. The organic phase was dried with sodium sulfate and the hexanes was removed under reduced pressure. The sample was then analyzed by GC-MS to determine the fatty acid compositions (FIG. 2). The sample was then analyzed by gas chromatography-mass spectroscopy (GC-MS) to determine the fatty acid compositions (i.e., FIG. 2, 3.82 wt % C16:0, 2.81 wt % C18:0, 83.5 wt % C18:1, 8.75 wt % C18:2, 0.23 wt % C20:0, 0.21 wt % C20:1, 0.72 wt % C22:0). The GC-MS was an Agilent 7890A GC system with a 5975S inert XL EI/CI MSD with triple-axis detector. The oven temperature profile was 70° C. for 2 minutes, ramp at 30° C./min to 165° C., and ramp at 0.5° C./min to 175° C. The column used was Agilent 122-5731 BD-5ht (400° C.: 30 m×250 µm×0.1 µm).

Zeolite treatment: Zeolite ammonium BETA was calcined in a furnace at 800° C. for 24 h followed by acid solution treatment with 1.0 N hydrochloric acid (HCl) in distilled water at 55° C. for 24 h. The treated zeolite was centrifuged at 3000 RPM for 30 minutes to remove the acid solution. The zeolite solid was washed with distilled water by stirring at RT for 30 minutes. The zeolite was centrifuged again and this process was repeated until the pH was neutral.

Isomerization, methylation and hydrogenation: The detailed procedures for these isomerization, methylation and hydrogenation steps were previously reported (Ngo, H. L., 2012; U.S. Pat. No. 9,115,076). Briefly, isomerization of sunflower oil was performed by mixing the oil (either 50 g or 200 g scale), zeolite (wt % to oil), distilled water (wt % to zeolite) in a 600 mL high pressure stainless-steel vessel equipped with a mechanical stirrer and an electric heating mantle with temperature controller. The stirred reactor was sealed, purged with Ar gas three times, jacketed with Ar, and heated to the desired reaction temperature. The pressure at a given reaction temperature would increase to 200 psi, depending on the catalyst and water used. At the end of a given reaction time, the reactor was cooled to RT and the pressure released. The mixture was filtered and was washed with ethyl acetate. The solvent in the filtrate was removed under reduced pressure to give a very complex mixture of oily product at quantitative yield 3).

After the isomerization reaction, small amounts of samples (typically <1 g) were methylated using 5 mL of methanol and 100 mg of sulfuric acid for FA analysis. The reaction was stirred for 2 h at 100° C. The workup procedures are similar to the published work (Ngo, H. L., 2012; U.S. Pat. No. 9,115,076). The methylated samples were then hydrogenated using 5 wt % Pd/C catalyst and methanol with hydrogen gas (15 psi $H_2$) at RT for 3 h. The hydrogenated product was vacuum filtered with celite to remove the catalyst. The solvent was removed under reduced pressure and the yields and conversions of the products were analyzed by GC-FID and GC-MS. The GC-FID used for this work was an Agilent 7890B instrument. The oven temperature profile was as follows: initial temperature 50° C., ramp at 15° C./min to 160° C., ramp at 7° C./min to 230° C., ramp at 30° C./min to 380° C., and hold for 10 min. The column used was an Agilent 123-5731, 2DB-5HT (0-400° C. (400° C.): 30 m×320 µm×0.1 µm) (Ngo, H. L., 2012; U.S. Pat. No. 9,115,076).

Figure 4:
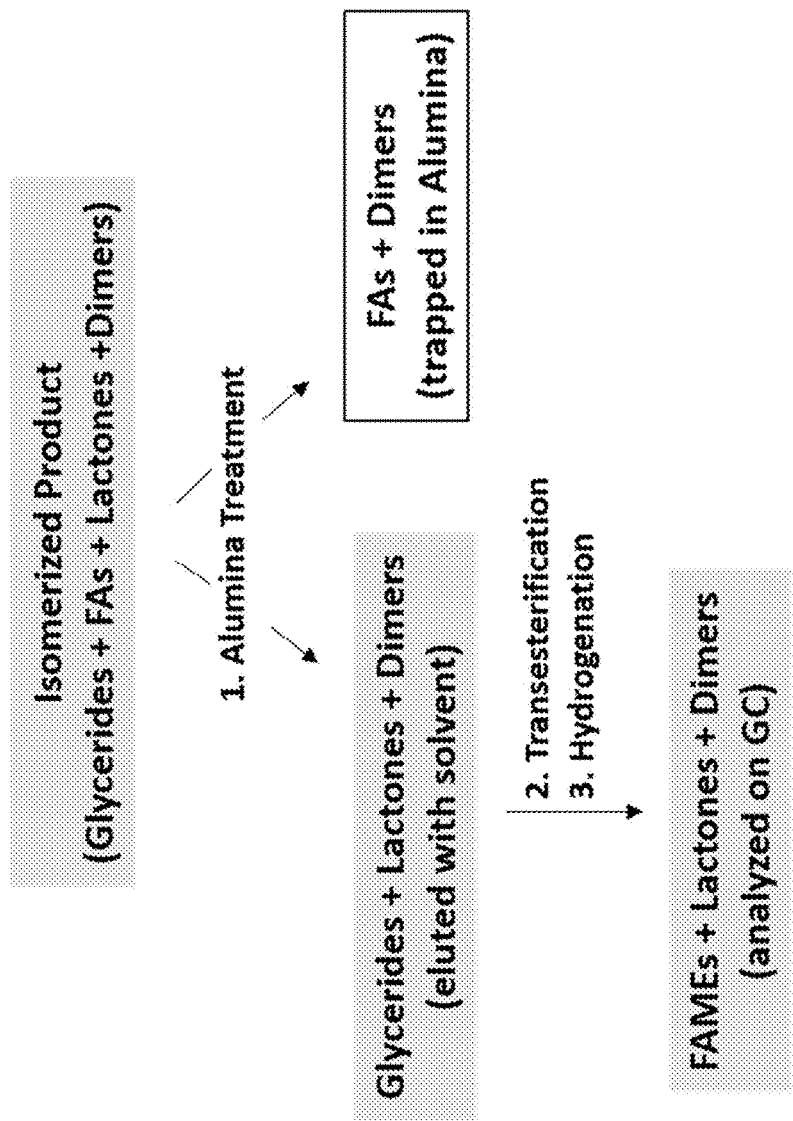
FIG. 4 shows a flow chart of the general three-step workup procedure for the isomerized products as described below.

To reduce the free FA content in the isomerized product, an alumina treatment method was used (FIG. 4). A suspension of alumina (20 g) in ethyl acetate (~20 mL) was added to a fritted funnel under vacuum to create a well-packed alumina layer. The oily sample (2.0 g) was diluted with ethyl acetate (~5 mL) and slowly added to the funnel. Once the sample was added, ethyl acetate (~40 mL) was added to the funnel to push the sample (i.e., glycerides) through. The solvent was removed under reduced pressure and the final product was run on the TAN (total acid number) instrument. Note that this alumina treatment method is generally only used for reactions that are run at small-scale so that the products can be analyzed more efficiently. For reactions that are performed at large-scale in which the products are isolated for application studies, the wiped-film distillation method is generally used.

Total acid number (TAN) was determined using a SI Analytics Titronic 500 (Xylem Global, Rye Brook, N.Y.). 50 mg of sample was added to a beaker that contained a stirring bar and then 10 mL of 1:1 toluene:isopropanol with 0.01% phenolphthalein was added to the beaker. The titrant (~0.05 N potassium hydroxide (KOH) in 19:1 methanol:water) was added to the beaker until the solution turned light pink. The amount of titrant used was recorded and the following calculation was used to obtain the TAN (all products were run in triple replicates):

$$TAN = \frac{v_{titrant} \times N_{titrant} \times MW_{KOH}}{w_{sample}(g)}.$$

Distillation of the isomerized branched-chain oil products: To efficiently remove the free FAs from the isomerized products at the large-scale level, a wiped film molecular distillation apparatus (VTA 1-5290, Verfahrenstechnische Anlagen GmbH & Co.KG, Germany) was used. 533.4 g of the sample was loaded on the feed vessel with temperature set at RT, the jacket or evaporator temperature was at 135° C. and the condenser bath temperature was at 55° C., vacuum pressure was set at 4.5 E-02 mbar (0.045 mbar or $4.5 \times 10^{-2}$ mbar or 0.00065 psi or $6.5 \times 10^{-04}$ psi), the feed rate was one drop of materials per second, and the wiper was set at 200 revolutions per minute (RPM). Under these conditions, two fractions were obtained. The light (more volatile) fraction contained lactones, LC-FA (linear-chain FA), MBC-FA, and dimers (248.3 g, 46.6%). While the heavy (less volatile) fraction contained the desired MBC-TG along with LC-TG, methyl-branched-chain diglycerides (MBC-DG), and linear-chain diglycerides (LC-DG) (276.2 g, 51.8%). 8.9 g (1.7%) of the product remained on the device and couldn't be removed, therefore this amount was not accounted for.

Normal phase HPLC with evaporative light-scattering detection was used to determine the ratio of the diglycerides and triglycerides (Haas, M. J., et al., JAOCS, 72: 519-525 (1995)). It was also used to confirm the presence of free fatty acids after the alumina treatment (Haas, M. J., et al., JAOCS, 72: 519-525 (1995)).

Characterization of the PXRD pattern was done on a Bruker d8 advanced diffractometer with a copper x-ray source (1.54 Angstrom). The spectra were collected from 2-30 2theta for a period of 18 minutes.

Results and discussion: In this isomerization reaction study, the sunflower oil with a total of 92.5 wt % unsaturated fatty acids (FIG. 2) could be converted into methyl-branched sunflower oil isomers (FIG. 3, structure 2, MBC-TG) in the presence of a modified $H^+$-BETA zeolite catalyst. The $H^+$-BETA catalyst was calcined at 800° C. for 24 h followed by dilute hydrochloric acid treatment. This BETA zeolite was chosen for trials because it has a larger pore size (channel axes: 7.6×6.4 Å) in comparison to the Ferrierite zeolite (channel axes: 5.4×4.2 Å) and the ZSM5 zeolite (channel axes: 5.6×5.3 Å). Without being bound by theory, this is suspected to make its framework more vulnerable to the high calcination temperature (e.g., 800° C.), and this vulnerability could provide greater amorphous open surface area to carry out the external isomerization of sunflower oil. Surprisingly, the use of this modified $H^+$-BETA zeolite catalyst did lead to the formation of these targeted MBC-TG products. Without being bound by theory, we suspect that the mechanism is different from the previously reported isomerization of fatty acids system (Ngo, H. L., 2012; U.S. Pat. No. 9,115,076) where branched-chain products were formed on the acid sites located inside the channels of the zeolites (Zhang, S., et al., Catal. Lett., 127: 33-38 (2009)). On the other hand, for the branched-chain oil products which we produced, they were probably formed on the acid sites located outside the zeolite channels. Although only one zeolite was tested in this study, other zeolites (e.g., ZSM5, Ferrierite, Zeolite Y) with high density of acid sites on the external surfaces would also be worthy to try with this concept for producing branched-chain oils. In general, as long as a solid catalyst contains acid sites on the surfaces then the branched-chain oil products should form. This discovery surprisingly opens up new chemistry for the formation of alkyl branched-chain products with oil feedstocks. Depending on the amount of water, catalyst loading, temperature and time, the reaction would produce different concentrations of oil isomers with a methyl group which could range from about 2 to about 20 wt %.

Figure 3:
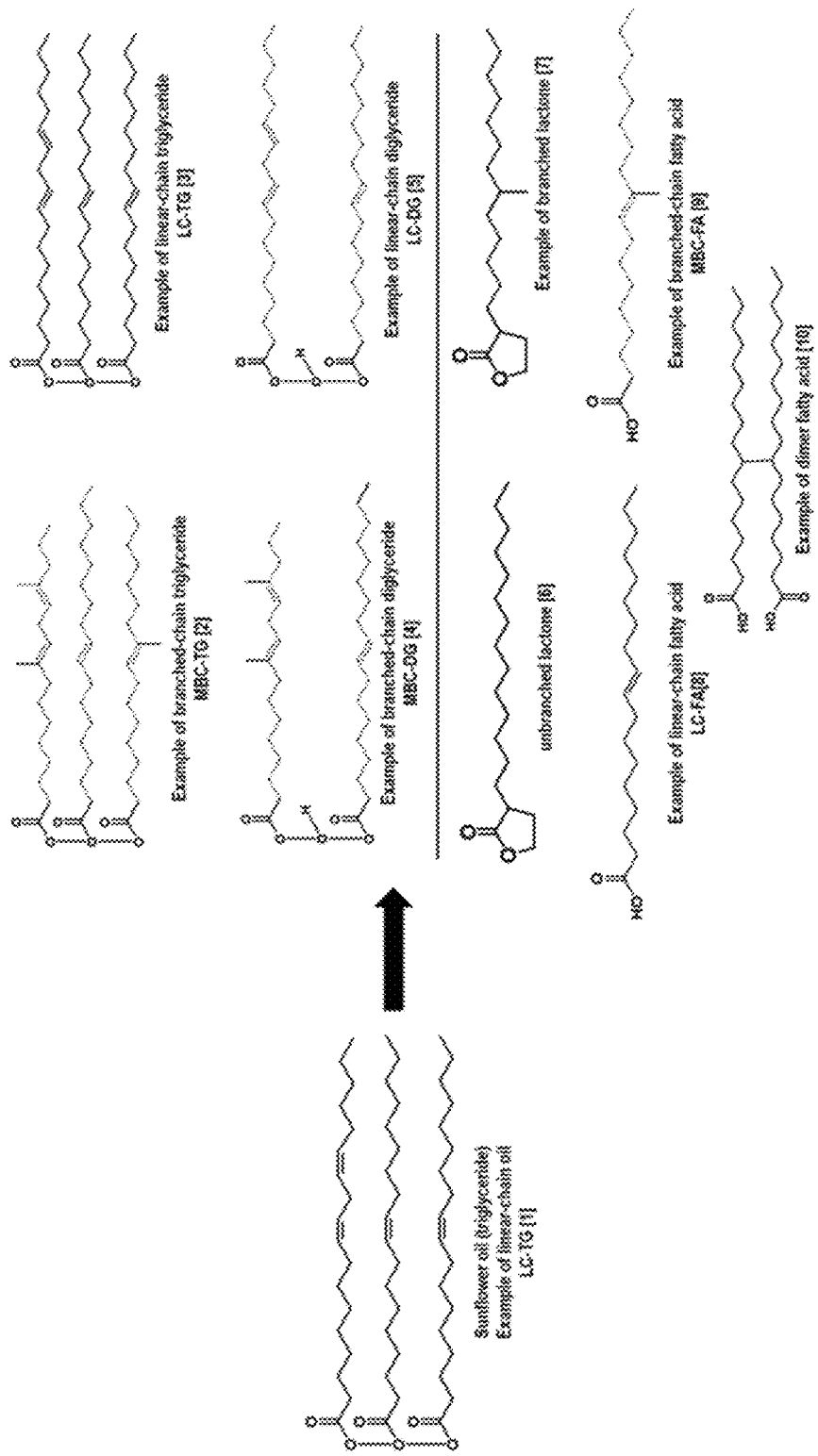
FIG. 3 shows one scheme for isomerization of sunflower oil to branched-chain sunflower oil as described below.

It should also be pointed out that the use of the $H^+$-BETA zeolite does not only yield the desired MBC-TG (FIG. 3, structure 2), but, in addition, surprisingly seven other types of isomeric by-products: branched-chain and/or linear-chain diglycerides (FIG. 3, structures 4&5, MBC-DG & LC-DG), branched-chain and/or linear-chain lactones (FIG. 3, structures 6&7), branched-chain and linear-chain fatty acids (FIG. 3, structures 8&9, MBC-FA & LC-FA), and dimer FA (FIG. 3, structure 10)) were produced because of the hydrolysis side reactions. Hydrolysis is unfortunately common with this type of reaction, especially when an oil and an acid zeolite with water are used at high temperatures (Ngaosuwan, K., et al., Ind. Eng. Chem. Res., 48: 4757-4767 (2009)). Being aware of the hydrolysis issue, when the isomerization reactions were carried out we spent tremendous research efforts on preventing the side reactions from occurring. A few control reactions with the sunflower oil were run without catalyst but with and without water at high temperatures. We thought these parameters would help determine the extent of the hydrolysis issue. Table 1 shows the reactions of the oil with and without water (no catalyst added) heated at 220° and 260° C. The oily products were then isolated and analyzed by an acid titrator device to determine the total acid number (TAN). This acid number tracked the formation of the FAs (FIG. 3, structures 8-10). The TAN results showed that hydrolysis occurred when water was present because a much higher TAN was observed (Entries 1&2). Although the temperature also influenced the outcome, it was surprisingly not as extreme as with water (Entries 3&4). With this information in mind, our experiments were carried out by optimizing the isomerization reaction with carefully calculated amount of water and temperature used. Linear-chain triglycerides (FIG. 3, structure 3, LC-TG) were also typically observed in the product mixture because the reaction does not give 100% branched glycerides. Therefore, any glycerides not converted to branched glycerides would also be observed in the product mixture. It is also important to note in FIG. 3 that although only one structure is shown for each product, in reality these products are not a single product; instead they are a mixture of many different isomers. This is surprisingly also an advantage as the heterogeneous complex mixture can give lower melting points, which was one of the goals of making these products.

Table 2 shows results of reactions run with 5 wt % modified $H^+$-BETA catalyst loading at different reaction temperatures, times, and with and without water added. The isomerized products were analyzed after they were subjected to FA removal with the alumina treatment method followed by transesterification and hydrogenation. This three-step workup was found to be necessary as the yields of glyceride products (or GC wt % composition) cannot be accurately determined on GC. FIG. 4 shows the flow chart of how the three step workup process works. First, the isomerized product was treated with alumina to separate the FAs (FIG. 3, structures 8&9). This treatment was to make sure that the branched-chain product comes from the glycerides. Second, the mixture containing glycerides, lactones and dimers was transesterified to give a mixture of unsaturated fatty acid methyl esters (UFAME) followed by hydrogenation to give the saturated FAME (SFAME) (Ngo, H. L., et al., 2012; U.S. Pat. No. 9,115,076; Ngo, H. L., et al., 2011; Ngo, H., et al., 2016). It was also important to note that although the lactones were found in the glyceride mixture after alumina treatment (FIG. 4), it was still reasonable to believe that these by-products did not form from glycerides because lactones are known to form through the migration of the carbocation to the gamma carbon of the fatty acid and then react with the carboxylic group (Zhang, S., et al., Catal. Lett., 127: 33-38 (2009)). As for the dimer by-products, without being bound by theory, it is possible that they were formed by self-coupling of either two FAs or two glycerides. As a result, the dimers were observed in both fractions after alumina treatment. Fortunately, these dimer by-products were surprisingly formed in a small amount and could be separated, so they are not as big of a concern.

Table 2, Entry 1 shows that when the reaction was run without water, only about 2.26 wt % branched-chain FAME (or branched glycerides) were obtained. Although the TAN value was moderate in comparison to the reactions run with water, the low percentages of branched-chain product indicated that water was needed. Entries 2&3 were reactions run with 40 wt % water at 260° C. for 8 h at two different pressures. These results showed that the pressures surprisingly made very little difference in these reactions. When the reaction was allowed to run for an additional 16 h, the branched-chain glycerides surprisingly increased slightly (Entry 4). Entry 5 reaction was different from the rest of the reactions as the $H^+$-BETA catalyst was only heated at 800° C. for 24 h (no acid solution treatment). This change was to see if the acid treatment step of the $H^+$-BETA catalyst was needed. However, the results obtained were surprisingly not as promising as only 5.10 wt % branched-chain glycerides and a much higher lactone level were produced. This indicated that the acid treatment of the zeolite was surprisingly needed to regenerate the acidic protons that were probably lost during calcination at 800° C. Even though the branched-chain glycerides were formed at 260° C., reactions at lower temperatures were explored to see if the hydrolysis issue could be avoided. As shown in Table 3, Entries 1-6, the reactions were run with and without water at 200° C. from 24 to 72 h. Without water, the reactions gave branched-chain results between 2.88 wt % and 5.06 wt % (Entries 1-3). With 10 wt % of water, surprisingly an increase in branched-chain glycerides was observed at 72 h (Entry 6). We also examined the reactions at 220° C. for the same amount of reaction times (Entries 7-12). Surprisingly, there seemed to be an increase in the branched-chain glycerides under these reaction conditions (i.e., up to 18.2 wt %, Entry 12). These isomerized results were quite interesting in terms of the maximum amounts of branched glycerides formed (Table 3, Entry 9). Without being bound by theory, this could be because the reactions were occurring on the external surfaces of the zeolite as the sunflower oil feedstock (i.e., triglyceride) was probably too bulky to undergo rearrangement of the double bond at the internal channels of the zeolites. This speculation could be true as the yield of the product surprisingly could not be obtained beyond 20 wt %, which, without being bound by theory, could be due to either limited amount of external acid sites on the zeolite available for isomerization or that the complex well-defined zeolite framework made it challenging for the oil to access. The latter was supported by the PXRD results (FIG. 1) which showed the zeolite framework was still highly crystalline even when this BETA zeolite was heated at 800° C. There was very little effect on the crystallinity of the solids.

Table 4 shows the exploration of the reproducibility and scale up probability of the reactions. Most importantly, these results were used to determine the cost modeling process which is explained in the next section. Entries 1-3 are repeated three reactions that ran at a fourfold increase compared to the reaction in Table 3, Entry 8. The results surprisingly showed that these reactions were reproducible and could be scaled up without much challenge. Entry 4 shows results from Entries 1-3 after the three sets of products were mixed together and purified (e.g., by wiped-film molecular distillation). After distillation, two major fractions were collected, and the light fraction as we expected contained MBC-FA, LC-FA, lactones, and dimer by-products in 46.6% yield. The heavy fraction contained the desired MBC-TG, LC-TG, MBC-DG and LC-DG which resulted in 51.8% yield. These percentages correspond to the calculated yield of the glycerides after alumina treatment. The heavy fraction was further analyzed on HPLC to determine the ratio between the TG and DG (data not shown), and the results showed an estimated ratio of about 70:30 of TG:DG. The HPLC results also determined the free fatty acids in the mixture. Interestingly, the HPLC results showed no sign of free fatty acids in the mixture; however, the TAN results were around 20 mg/KOH (data not shown). Without being bound by theory, this high TAN was suspected to be due to some sort of acid organic compounds which perhaps came from the HCl treatment of the zeolite. These compounds were removed by the alumina treatment which bought the TAN down to 0.99 mg/KOH (Entry 4). Another important finding from this distillation step was that the lactone level dropped significantly after distillation (less than 2.51 wt %). This further confirmed that the lactones must have come from FAs (Entry 4).

Conclusions: One objective of this research was to introduce branching on the alkyl chain of the oil (composed almost entirely of triglycerides) with the goal of improving its low-temperature property for use, for example, in the oleochemical industry. Even though this isomerization reaction did not give complete methyl branching double bond and thereby leaving behind some unbranched double bonds at the internal location of the fatty acids in the glyceride mixture, this newly developed mixture could be utilized under similar conditions as the parent glycerides (i.e., unbranched double bonds) to make new kinds of larger molecular weight products to be explored in the biopolymer and biolubricant industries.

All of the references cited herein, including U.S. Patents and U.S. Patent Application Publications, are incorporated by reference in their entirety. Also incorporated by reference in their entirety are the following U.S. Pat. Nos. 9,115,076; 8,748,641; 7,534,917; 6,878,838; and 6,831,184. Also incorporated by reference in their entirety are the following: U.S. Patent Application Publication 2011/0263884; U.S. Patent Application Publication 2018/0186716; and Ha, L., et al., Applied Catalysis A: General., 356: 52-56 (2009).

Thus, in view of the above, there is described (in part) the following:

A method for preparing triglyceride oils containing at least 2% branching on the hydrocarbon chain, said method comprising (or consisting essentially of or consisting of) subjecting in a pressurized container (a) a feedstock containing unsaturated fatty acids attached to a glycerol backbone having 6 to 25 carbon atoms or mixtures thereof, (b) modified zeolite, and (c) water or alcohol in the presence of an inert atmosphere (e.g., at a temperature of about 150° C. to about 350° C. and a pressure of about 10 to about 300 psi for about 24 to about 72 hours) to produce triglycerides containing at least 2% branching (and optionally isolating said triglycerides containing at least 2% branching and purifying the isolated triglycerides containing at least 2% branching); wherein said modified zeolite has been calcined at about 760° C. to about 840° C. for about 20 to about 28 hours, then placed in about 1N HCl at about 50° C. to about 60° C. for about 20 to about 28 hours and washed with water (e.g., distilled) until the pH is neutral. The above method where said water or alcohol is about 5 to about 40 wt % to said zeolite. The above method, said method further comprising optionally isolating said triglycerides containing at least 2% branching and optionally purifying the isolated triglycerides containing at least 2% branching. The above method, said method comprising subjecting in a pressurized container (a) a feedstock containing unsaturated fatty acids attached to a glycerol backbone having 6 to 25 carbon atoms or mixtures thereof, (b) modified zeolite, and (c) water or alcohol in the presence of an inert atmosphere at a temperature of about 150° C. to about 350° C. The above method, wherein said temperature is about 175° C. to about 325° C. The above method, wherein said zeolite has a pore size (channel axes) of at least about 7.6×6.4 Å. The above method, wherein said method produces less than about 6 wt % dimers.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein. Thus, the specification includes disclosure by silence ("Negative Limitations In Patent Claims," AIPLA Quarterly Journal, Tom Brody, 41(1): 46-47 (2013):

> . . . Written support for a negative limitation may also be argued through the absence of the excluded element in the specification, known as disclosure by silence . . .
> Silence in the specification may be used to establish written description support for a negative limitation. As an example, in Ex parte Lin [No. 2009-0486, at 2, 6 (B.P.A.I. May 7, 2009)] the negative limitation was added by amendment . . . In other words, the inventor argued an example that passively complied with the requirements of the negative limitation . . . was sufficient to provide support . . .
> This case shows that written description support for a negative limitation can be found by one or more disclosures of an embodiment that obeys what is required by the negative limitation . . . .

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Hydrolysis studies of sunflower oil at various reaction conditions without H+-BETA catalyst.[a]

| Entry | Distilled Water [wt % to oil] | Temp. [° C.] Time [h] | Pressure [psi] | TAN [mgKOH/g sample] |
|---|---|---|---|---|
| 1 | 0 | 220 24 | 18 | 1.03 |
| 2 | 2.0 | 220 24 | 18 | 19.3 |
| 3 | 0 | 260 24 | 8.0 | 8.86 |
| 4 | 2.0 | 260 24 | 27 | 26.4 |

[a]All reactions were performed with sunflower oil (50 g) in a 600 mL high pressure stainless steel reactor.
TAN = total acid number

TABLE 2

Isomerization of sunflower oil with H+-BETA zeolite and various reaction conditions.[a]

| | | | | | GC-FID wt % Compositions | | | | |
|---|---|---|---|---|---|---|---|---|---|
| Entry | Distilled Water [wt % to zeolite] | Temp. [° C.] Time [h] | Pressure [psi] | TAN [mgKOH/g sample] | Linear-chain FAME $C_{16:0}$ | Branched-chain FAME $C_{18:0}$ | Linear-chain FAME $C_{18:0}$ | Branched-chain & Linear-chain lactones | Dimer FAME |
| 1[b] | 0 | 220 24 | 17 | Before FA removal = 55.6 After FA removal = 0.83 | 4.73 | 2.26 | 84.1 | 6.36 | 2.55 |
| 2[b] | 40 | 260 8 | 24 | Before FA removal = 115 After FA removal = 2.96 | 4.37 | 17.9 | 61.2 | 11.75 | 4.78 |
| 3[b] | 40 | 260 8 | 255 | Before FA removal = 121 After FA removal = 1.75 | 4.21 | 14.0 | 66.6 | 13.2 | 2.01 |
| 4[b] | 40 | 260 24 | 32 | Before FA removal = 116 After FA removal = 0.28 | 4.60 | 21.3 | 51.6 | 16.9 | 5.64 |
| 5[c] | 40 | 260 8 | 24 | Before FA removal = 103 After FA removal = 0.10 | 4.73 | 5.10 | 53.8 | 31.3 | 5.14 |

[a]All reactions were performed with sunflower oil (50 g) and H+-BETA zeolite (5 wt % to oil) in a 600 mL high pressure stainless steel reactor. Isomerized products were transesterified and hydrogenated before analysis. Tridecanote fatty acid methyl ester ($C_{13:0}$) was used as an internal standard.
[b]H+-BETA zeolite was prepared by heating the parent BETA at 800° C. for 24 h, treating with HCl at 55° C. for 24 h, and heating in furnace at 120° C. for 3 h.
[c]H+-BETA zeolite was prepared by heating the parent BETA at 800° C. for 24 h.

TABLE 3

Isomerization of sunflower oil with H+-BETA zeolite catalyst.[a]

| | | | | | GC-FID wt % compositions | | | | |
|---|---|---|---|---|---|---|---|---|---|
| Entry | Distilled Water [wt % to zeolite] | Temp [° C.] Time [h] | Pressure [psi] | TAN [mgKOH/g sample] | Linear-chain FAME $C_{16:0}$ | Branched-chain FAME $C_{18:0}$ | Linear-chain FAME $C_{18:0}$ | Branched-chain & Linear-chain lactones | Dimer FAME |
| 1 | 0 | 200 24 | 14 | Before FA removal = 32.6 After FA removal = 0.48 | 4.48 | 2.88 | 85.60 | 4.03 | 2.99 |
| 2 | 0 | 200 48 | 42 | Before FA removal = 37.0 After FA removal = 0.87 | 4.67 | 2.84 | 79.9 | 6.99 | 5.60 |
| 3 | 0 | 200 72 | 42 | Before FA removal = 50.2 After FA removal = 0.61 | 4.88 | 5.06 | 78.4 | 7.98 | 3.68 |
| 4 | 10 | 200 24 | 3 | Before FA removal = 40.3 After FA removal = 0.99 | 4.40 | 2.05 | 88.2 | 2.92 | 2.43 |
| 5 | 10 | 200 48 | 35 | Before FA removal = 50.8 After FA removal = 1.03 | 4.98 | 2.36 | 45.4 | 36.13 | 11.08 |
| 6 | 10 | 200 72 | 35 | Before FA removal = 61.8 After FA removal = 1.53 | 4.63 | 9.01 | 76.69 | 6.14 | 3.51 |
| 7 | 5.0 | 220 24 | 75 | Before FA removal = 66.9 After FA removal = 3.40 | 5.54 | 8.61 | 76.1 | 7.66 | 2.09 |
| 8 | 5.0 | 220 48 | 74 | Before FA removal = 84.4 After FA removal = 1.93 | 4.67 | 13.9 | 66.7 | 10.4 | 4.37 |
| 9 | 5.0 | 220 72 | 75 | Before FA removal = 93.7 After FA removal = 1.51 | 4.82 | 20.1 | 50.5 | 18.3 | 6.27 |
| 10 | 10 | 220 6 | 40 | Before FA removal = 40.5 After FA removal = 0.48 | 4.56 | 2.91 | 84.1 | 6.01 | 2.42 |

TABLE 3-continued

Isomerization of sunflower oil with H⁺-BETA zeolite catalyst.[a]

| | | | | | GC-FID wt % compositions | | | | |
|---|---|---|---|---|---|---|---|---|---|
| Entry | Distilled Water [wt % to zeolite] | Temp [° C.] Time [h] | Pressure [psi] | TAN [mgKOH/g sample] | Linear-chain FAME $C_{16:0}$ | Branched-chain FAME $C_{18:0}$ | Linear-chain FAME $C_{18:0}$ | Branched-chain & Linear-chain lactones | Dimer FAME |
| 11 | 10 | 220 24 | 80 | Before FA removal = 77.9 After FA removal = 1.75 | 5.44 | Didn't determine 7.97 | 73 | 9.63 | 3.96 |
| 12 | 10 | 220 48 | 40 | Before FA removal = 93.9 After FA removal = 0.64 | 4.38 | Didn't determine 18.2 | 54.8 | 16.7 | 5.96 |

[a]All reactions were performed with sunflower oil (50 g) and H⁺-BETA zeolite (10 wt % to oil) in a 600 mL high pressure stainless steel reactor. H⁺-BETA zeolite was prepared by heating the parent BETA at 800° C. for 24 h, treating with HCl at 55° C. for 24 h, and heating in furnace at 120° C. for 3 h. Isomerized products were transesterified and hydrogenated before analysis. Tridecanote fatty acid methyl ester ($C_{13:0}$) was used as an internal standard.

TABLE 4

Demonstration of the isomerization reaction's reproducibility, scale up and distillation.[a]

| | | GC-FID wt % Compositions | | | | |
|---|---|---|---|---|---|---|
| Entry | TAN [mgKOH/g sample] | Linear-chain FAME $C_{16:0}$ | Branched-chain FAME $C_{18:0}$ | Linear-chain FAME $C_{18:0}$ | Branched-chain & Linear-chain lactones | Dimer FAME |
| 1 | Before FA removal = 103 After FA removal = 1.69 | 4.10 | 13.0 | Didn't determine 51.6 | 27.0 | 4.29 |
| 2[b] | Before FA removal = 106 After FA removal = 1.97 | 5.12 | 14.8 | Didn't determine 46.5 | 28.3 | 5.32 |
| 3[b] | Before FA removal = 115 After FA removal = 1.98 | 4.78 | 11.7 | Didn't determine 43.4 | 36.4 | 3.71 |
| 4[c] | After FA removal = 0.99 | 5.68 | 15.0 | 73.3 | 2.51 | 3.51 |

[a]All reactions were performed with sunflower oil (200 g), H⁺-BETA zeolite (10 wt % to oil), distilled water (5.0 wt % to zeolite) in a 600 mL high pressure stainless steel reactor at 220° C. for 48 h under 75 psi N₂ pressure. H⁺-BETA zeolite was prepared by heating the parent BETA at 800° C. for 24 h, treating with HCl at 55° C. for 24 h, and heating in furnace at 120° C. for 3 h. Isomerized products were transesterified and hydrogenated before analysis. Tridecanote fatty acid methyl ester ($C_{13:0}$) was used as an internal standard.
[b]Replicate of Entry 1.
[c]A combination of three isomerized products from Entries 1-3, purified on wiped-film molecular distillation followed by alumina treatment.

We claim:

1. A method for preparing triglyceride oils containing at least 2% branching on the hydrocarbon chain, said method comprising subjecting in a pressurized container (a) a feedstock containing unsaturated fatty acids attached to a glycerol backbone having 6 to 25 carbon atoms, or mixtures thereof, (b) modified zeolite, and (c) water or alcohol in the presence of an inert atmosphere to produce triglycerides containing at least 2% branching; wherein said modified zeolite has been calcined at about 760° C. to about 840° C. for about 20 to about 28 hours, then placed in about 1N HCl at about 50° C. to about 60° C. for about 20 to about 28 hours and washed with water until the pH is neutral.

2. The method according to claim 1, said method further comprising optionally isolating said triglycerides containing at least 2% branching and optionally purifying the isolated triglycerides containing at least 2% branching.

3. The method according to claim 1, said method comprising subjecting in a pressurized container (a) a feedstock containing unsaturated fatty acids attached to a glycerol backbone having 6 to 25 carbon atoms or mixtures thereof, (b) modified zeolite, and (c) water or alcohol in the presence of an inert atmosphere at a temperature of about 150° C. to about 350° C.

4. The method according to claim 3, wherein said temperature is about 175° C. to about 325° C.

5. The method according to claim 3, wherein said temperature is about 200° C. to about 300° C.

* * * * *